United States Patent
Schmitz

(10) Patent No.: US 6,563,909 B2
(45) Date of Patent: May 13, 2003

(54) X-RAY EXAMINATION APPARATUS

(75) Inventor: Georg Schmitz, Roetgen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/741,975

(22) Filed: Dec. 20, 2000

(65) Prior Publication Data

US 2001/0050974 A1 Dec. 13, 2001

(30) Foreign Application Priority Data

Dec. 23, 1999 (DE) .......................... 199 62 281

(51) Int. Cl.$^7$ .................................. G21K 3/00
(52) U.S. Cl. ....................... 378/156; 378/145
(58) Field of Search ...................... 378/147, 148, 378/149, 150, 151, 156, 157, 158, 159, 145

(56) References Cited

U.S. PATENT DOCUMENTS

| 5,170,425 A | 12/1992 | Haendle ............... 378/151 |
| 5,287,396 A | 2/1994 | Stegehuis ................ 378/98 |
| 5,394,454 A * | 2/1995 | Harding ................ 378/86 |
| 6,188,749 B1 * | 2/2001 | Schiller et al. ........... 378/158 |
| 6,252,939 B1 * | 6/2001 | Young et al. ............. 378/156 |

FOREIGN PATENT DOCUMENTS

| EP | 0496438 A1 | 1/1992 | ........... A61B/6/06 |
| EP | 0981999 A2 | 8/1999 | ........... A61B/6/03 |

* cited by examiner

Primary Examiner—Drew A. Dunn
Assistant Examiner—Jurie Yun
(74) Attorney, Agent, or Firm—John Vodopia

(57) ABSTRACT

The invention relates to an X-ray examination apparatus which includes an X-ray source, an X-ray detector, absorption means arranged between the X-ray source and the X-ray detector, a control unit for adjusting the absorption degree of the absorption means, an image processing unit and a display unit. In order to perform an automatic adjustment of the absorption means, the absorption degree therein is optimized in dependence on user-specific parameters ($\underline{r}$) and/or apparatus-specific parameters ($\underline{s}$) and/or structure parameters ($\underline{C}$) and/or parameters ($\underline{r}$) classifying the subject matter of the image.

3 Claims, 2 Drawing Sheets

X-RAY EXAMINATION APPARATUS

The invention relates to an X-ray examination apparatus which includes an X-ray source, an X-ray detector, an absorption means arranged between the X-ray source and the X-ray detector, a control unit for adjusting the degree of absorption of the absorption means, an image processing unit and a display unit.

Absorption means are used to limit the X-ray beam path in X-ray examination apparatus. To this end, the means is arranged between the X-ray source and the X-ray detector. On the one hand, limiting the X-ray beam path limits the region of the patient to be irradiated to a necessary optimum. On the other hand, such limiting limits the X-ray image to be diagnosed by the physician to the region with the organ to be examined, without imaging additional regions that do not provide useful information but could affect the quality of the X-ray image.

U.S. Pat. No. 5,287,396 discloses an X-ray apparatus with absorption means. The X-ray examination apparatus therein includes an image processing unit with a memory in which the absorption values of an X-ray image are stored in the form of a matrix. The X-ray image is segmented into sub-regions by means of detection means. The image is subdivided into a foreground and a background on the basis of a threshold value for the absorption value. The position of the absorption means is calculated by means of an arithmetic unit and the subdivision. The absorption means are then shifted to the calculated position by means of a drive unit. The absorption means are automatically positioned in such a manner that the surface area of the covered background is maximum while the surface area of the covered foreground is minimum.

The described automatic positioning of the absorption means has the drawback that the image is subdivided or segmented into two binary classes. The absorption means are positioned on the basis of this subdivision. This type of segmentation constitutes an unnecessary limitation for the calculation of the position of the absorption means, because not only the local image brightness is decisive for the positioning of the absorption means. Absorption means often exhibit a weak attenuation at their edges, so that the X-ray image is attenuated less when diagnostically relevant regions are covered. This fact is not taken into account in U.S. Pat. No. 5,287,396.

In the case of manual adjustment of the absorption means by a physician, further information is used for adjustment. In the end the physician finds a compromise between all parameters taken into account.

In contemporary systems positioning is performed either directly manually, mechanically or by motor-driven positioning to a position selected manually on the basis of an image impression. This manual adjustment requires an examination time, is disturbing to the physician and distracts the attention from the actual examination and the care of the patient.

Therefore, it is an object of the invention to provide an X-ray examination apparatus in which the absorption degree of the absorption means is automatically optimally adjusted.

This object is achieved in that the absorption degree is optimized in dependence on user-specific parameters, apparatus-specific parameters, structure parameters or parameters classifying the subject matter of the image.

The X-rays emitted by the X-ray source pass the absorption means and irradiate the patient. The X-ray image produced by the X-rays is imaged on an X-ray detector. After conversion into an electric image signal, the X-ray image is transferred to an image processing unit in which it is stored; it is displayed on a monitor at the same time.

For medical X-ray examinations the absorption means are positioned during an X-ray exposure in such a manner that the radiation is attenuated or stopped in image regions in which the detector was struck by direct X-rays that have not been attenuated by the patient, thus avoiding disturbing over-exposures, that the X-rays are attenuated in diagnostically irrelevant regions so as to avoid an unnecessary patient dose as well as scattered radiation, and that the X-rays are not stopped in diagnostically relevant regions, for example, regions containing anatomical structures, thus enabling optimum diagnostic use. These steps lead to an optimized image quality and patient dose.

The following parameters can be classified for the adjustment of the absorption means. The basis for optimum adjustment is formed by the opinion of the physician performing the diagnosis as to how the X-ray image should be. This opinion is gathered in the user-specific parameters. The apparatus-specific parameters contain information such as the type of X-ray examination apparatus, tube voltage, tube current and exposure time. Structure parameters are values determined from the X-ray image. Structure parameters contain information as regards the grey scale value distribution in a group of pixels. Structure parameters also contain information concerning the image contrast. To this end, a histogram is formed of the grey scale values of the entire image; the appearance of the relevant grey scale values is taken up in said histogram. The distribution then obtained can be used as a measure of the contrast. The parameters classifying the subject matter of the image contain information concerning the organ or the body region to be irradiated by means of X-rays. The user-specific parameters and the parameters classifying the subject matter of the image are combined so as to form a knowledge base.

The image processing unit is provided with arithmetic means whereto said parameters are applied and which calculate an optimum adjustment of the absorption means on the basis of said parameters. The parameters are stored in memories or are extracted from the acquired X-ray image. The parameters are combined in a quality function which is optimized in a manner to be specified. The adjustment thus calculated is applied to the control unit via which the absorption means are moved to the calculated position or via which the absorption means adopt the calculated adjustment.

The absorption means in an embodiment of the X-ray examination apparatus according to the invention are essentially not transparent to X-rays. The absorption means can advantageously induce an absorption which is not one hundred percent, so that a smooth transition occurs between the exposed region and the covered region in the X-ray image. To this end, for example, the absorption means are shaped as a wedge so that absorption at the tip of the wedge is not total. This variation of the attenuation is also taken up in the knowledge base.

The absorption means can be arranged in a diaphragm device in such a manner that they are moved to the calculated position by means of sliding devices which are electrically or hydraulically driven. The described wedges or diaphragm plates are then used. The absorption means are arranged in such a manner that they are capable of limiting the conical X-ray beam path from all sides or that they limit the X-ray beam path in one location only by partial insertion of a single diaphragm plate.

A further embodiment of the X-ray examination apparatus according to the invention utilizes a filter consisting of a plurality of filter elements that can be filled as the absorption means. Therein, the degree of filling of a liquid attenuating X-rays can be electrically adjusted. An X-ray attenuation which varies across the beam cross-section can thus be realized.

It has been found that it is advantageous to superpose a calculated adjustment of the absorption means on the rendition of the X-ray image on the monitor before performing the ultimate adjustment by means of the control unit. The attending physician can thus evaluate and possibly correct the calculated adjustment.

It has also been found that the variations of the parameters are advantageously stored so as to collect empirical values and to adapt the parameters of the knowledge base on the basis of these empirical values. The degree of adaptation can then be adjusted. This results in a learning process which ultimately enables faster, automatic and more correct adjustment of the absorption means.

The following description deals with the combining of the parameters in a quality function Z and with their optimization. The parameters for the adjustment of the absorption means are taken up in an adjustment parameter vector $\underline{p}_{akt}$. These parameters may be, for example an angle and the insertion length of a semi-transparent diaphragm plate.

The attenuation effect of the adjustment of the absorption means used in the actual X-ray image can be calculated by simulation, for example by means of X-ray beam tracking, and be removed by division from the X-ray image stored in the image processing unit.

The image processing unit calculates parameters characterizing the image contents from the resultant image for N different image regions M. Generally speaking, these image regions will be rectangles which adjoin one another in a gapless or overlapping manner. The parameters characterizing the image are, for example, the mean brightness or degrees of image contrast and structure contained. All calculated parameters are combined in an M×N parameter matrix $\underline{\underline{C}}$. The contrast can be determined, for example by variance calculation. A parameter calculation based on Haralick (IEEE 67(5): 610–621, 1979), describing statistical and structural methods concerning texture or condition of images, can also be used.

As an alternative for such direct calculation of the parameters, the parameters of the matrix $\underline{\underline{C}}$ can be calculated directly from the image stored in the image memory and the effect of the actual attenuation by the absorption means can be taken into account by a correction of the parameters. For the above-mentioned exemplary parameter concerning the mean brightness such a correction possibility is provided by division of the mean brightness by the mean attenuation.

The attenuation D of the absorption means will now be calculated in dependence on possibly novel adjusting parameters. The novel adjusting parameters to be tested are combined in the adjustment parameter vector $\underline{p}$.

The parameter matrix $\underline{\underline{C}}$ and the attenuation D can now be taken into account for evaluating the quality of the effect of the absorption means. To this end, a suitable quality function Z is calculated; this function may be parameterized by a plurality of factors characterizing the desired image quality, for example by weighting for different image quality standards or parameters. The parameters of the quality function Z, characterizing the behavior of the function Z in dependence on the function arguments, are combined in the vector $\underline{r}$. The user-specific parameters and the parameters classifying the subject matter of the exposure are taken up in the vector $\underline{r}$. User-specific parameters contain, for example preferences of given operators for the rendition of the partly covered X-ray image. Parameters characterizing the subject matter of the exposure contain information as regards the type of exposure. In the case of an X-ray image of the heart, for example, the very brightly reproduced lung is imaged around the heart to be diagnosed. This knowledge is taken up in the parameters classifying the subject matter of the exposure as they are included, like the user-specific parameters, in the vector $\underline{r}$ forming the knowledge base.

The apparatus-specific parameters are combined in the system parameter vector $\underline{s}$. The actual state of the X-ray examination apparatus, or parameters calculated therefrom, are taken up in the system parameter vector $\underline{s}$. For example, this may be the X-ray dose applied for the actual image. A dose-dependent grey scale threshold for overexposed region can be taken up as a derived parameter in this system parameter vector $\underline{s}$.

The quality function Z can be derived either heuristically or via rule-based methods such as, for example, those of fuzzy logic. It is also possible to realize the quality function as a neural network which is trained on representative image data and desired adjustments of the absorption means prior to putting the X-ray examination apparatus into operation.

More generally speaking, any linear or non-linear function approximator can be used that approximates the desired behavior on the basis of training input data and training output data. The vector $\underline{r}$ parameterizes the adjusting rule and hence constitutes the knowledge base or control base of the system.

In order to calculate an optimum diaphragm position or optimum adjustment of the absorption means, use is made of an optimization method which varies the adjustment parameter vector $\underline{p}$ and determines each time the attenuation D and therefrom the function value Z(D,r,s). For the optimization method use can be made, for example, of a simple algorithm such as the Nelder-Mead Simplex method (Nelder, J. A. and Mead, R. 1965, Computer Journal, vol. 7, pp. 308–313). The optimization result is the optimized adjustment of the absorption means which is contained in the adjustment parameter vector $\underline{P}_{opt}$.

$$\underline{p}_{opt} = \arg\operatorname{opt}_{\underline{p}} Z(r, s, \underline{\underline{C}}, D(\underline{p})) \tag{1}$$

This adjustment of the absorption means can be realized directly automatically via a control unit. Alternatively, the absorption means in the form of plates or plate edges can be graphically superposed on the monitor image. The operator thus has the possibility of correction and confirmation. The new actual adjustment $\underline{P}_{akt}$ can again be used to adapt the knowledge base, represented in the vector $\underline{r}$, to the user behavior. This can be realized via renewed training of the learning system used. The following simple adaptation of the control base, however, is also possible:

for the corrected adjustment $\underline{p}_{akt}$ the function Z is optimized in dependence on the knowledge base r:

$$r_{opt} = \arg\operatorname{opt}_{\underline{r}} Z(r, s, \underline{\underline{C}}, D(\underline{p}_{akt})) \tag{2}$$

Depending on the quality function, the optimization may be a maximization or a minimization. The new control base $\underline{r}'$ is then determined via a learning step:

$$\underline{r}' = \underline{r} + \alpha(\underline{r}_{opt} - \underline{r}) \tag{3}$$

Therein, α represents the learning rate which is situated in the interval [0,1]. For α=1 the system is adapted in a hop-like manner; the system is not adaptive for α=0. Generally speaking, small values are used for α. The adaptation is performed in a user-specific manner and is stored in a database for different users and applications. Such parameters are taken up in the vector r.

In comparison with the X-ray examination apparatus described in the state of the art the X-ray examination apparatus according to the invention can also offer an evaluation of the quality of partial coverages of relevant objects as a result of the absence of binary segmentation in background and image contents and the evaluation performed instead of the overall image quality of a virtual image with positioned diaphragm. The operator can thus define the permitted degree of coverage by adjustment of only a single parameter, for example, when the quality function is suitably chosen. This adjustment can be adapted and stored in a user-specific and application-specific manner.

An embodiment of the invention will be described in detail hereinafter with reference to the drawings. Therein:

Figure 1:
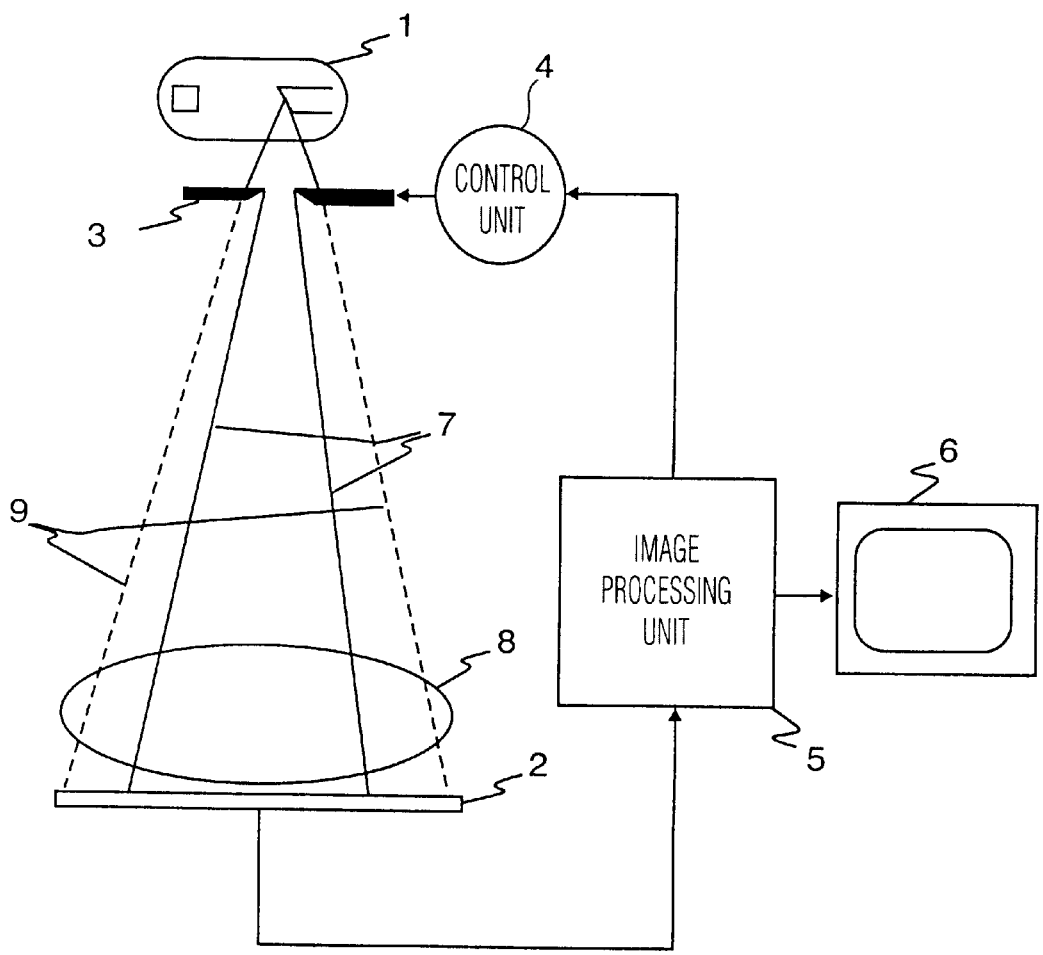
FIG. 1 shows diagrammatically an X-ray examination apparatus.

FIG. 1 shows the construction of the X-ray examination apparatus according to the invention. The X-ray source 1 emits X-rays 9. The X-rays pass the absorption means 3 which will also be referred to hereinafter as collimator plates 3. The collimator plates 3 are displaced by the control unit 4. The X-rays 7 transmitted by the collimator plates 3 irradiate the object 8 to be examined and are incident on the X-ray detector 2. The X-ray image is then picked up and converted into an electric image signal. The image signal 20 is applied to the image processing unit 5. The acquired image is displayed on the display unit in the form of a monitor 6. The image processing unit 5 is connected to the control unit 4 in order to adjust the degree of absorption of the collimator plates 3.

Figure 2:
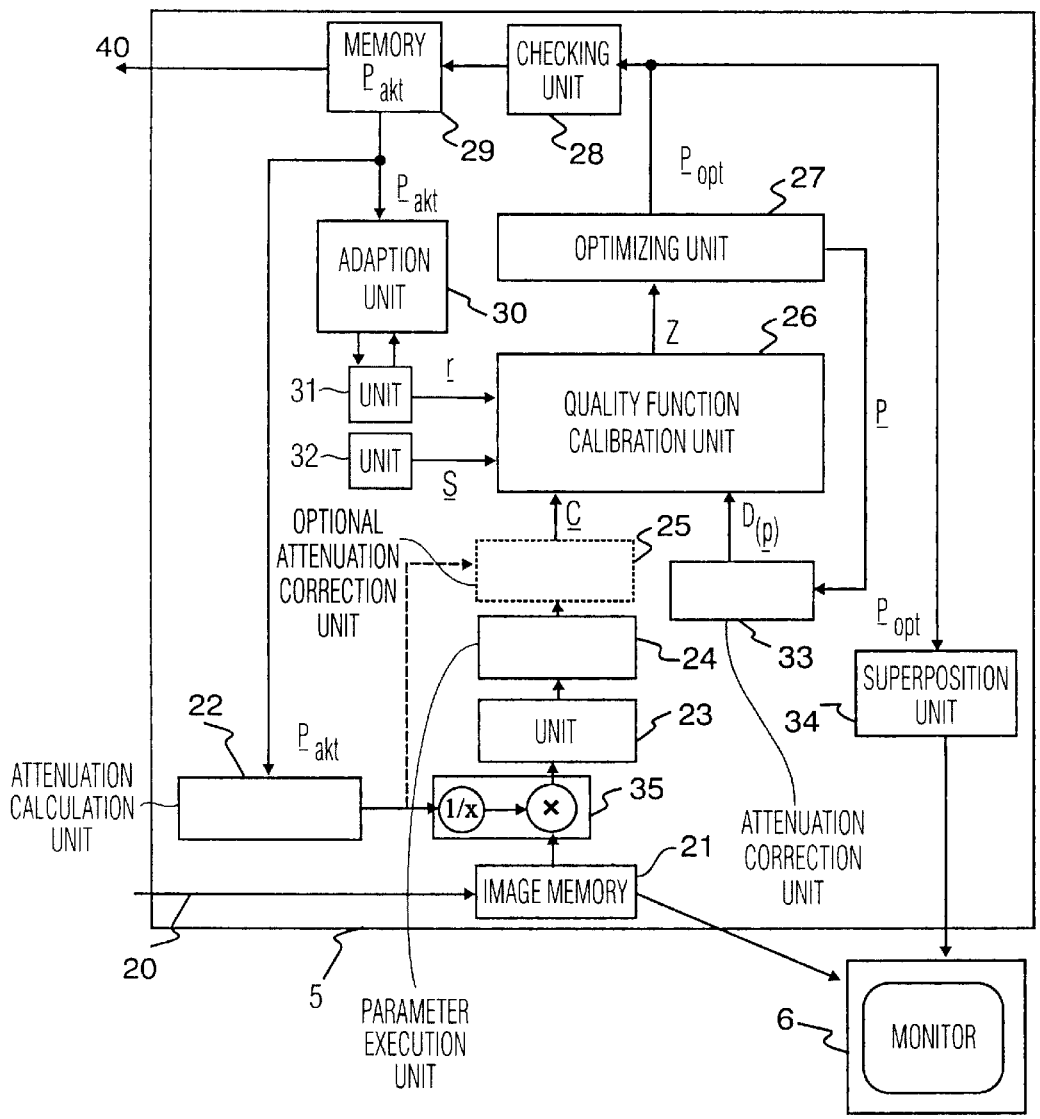
FIG. 2 shows the construction of the image processing unit.

FIG. 2 shows the construction of the image processing unit 5. The image processing unit 5 receives the image signal 20 from the X-ray detector 2 which is not shown herein. The signal is applied to the image memory 21 for storage and at the same time to the monitor 6 for display. The actual attenuation is calculated in the attenuation calculation unit 22 by means of the adjustment parameter vector $\underline{p}_{akt}$ stored in the memory 29. The actual attenuation $D(\underline{p}_{akt})$ is the value of the attenuation applied to the acquired X-ray image, because absorption means may have been partly slid into the X-ray beam path. The unit 35 forms the reciprocal value of the actual attenuation value D in order to multiply it by the X-ray image stored in the image memory 21 so as to obtain an image wherefrom the attenuation D has been removed.

The non-attenuated image is subdivided into image regions N in the unit 23. The unit 23 is succeeded by a parameter extraction unit 24 for calculating the image parameters such as contrast or structure parameters. In the optional attenuation correction unit the attenuation could also be calculated on the basis of the adjustment parameter vector $\underline{P}_{akt}$. The parameter matrix $\underline{\underline{C}}$ thus formed is applied to the quality function calculation unit 26. The unit 26 receives from the unit 32 the system parameters in the form of the system parameter vector s and the vector r representing the knowledge base. The knowledge or control base in the form of the vector r is stored in the unit 31 and is applied to the unit 26 for the calculation of the quality function Z as well as to the adaptation unit 30 for the adaptation of the knowledge base.

The quality function is optimized in the unit 27. The adjusting parameter vector $\underline{p}_{opt}$ is calculated which contains the optimized adjustment of the absorption means. This adjustment parameter vector $\underline{p}_{opt}$ is applied to a further attenuation correction unit 33 which is similar to the attenuation unit 22 and calculates the adjustment of the attenuation $D(\underline{p})$ on the basis of the adjustment parameter vector $\underline{p}_{opt}$ in order to apply it to the calculation of the quality function in the unit 26 again so as to be used for further optimization of the adjustment parameter vector p during the next run, until the optimized adjustment parameter vector $\underline{p}_{opt}$ has been determined. The latter is then applied to the unit 28 in which it is checked or confirmed that the instantaneous adjustment of the plates, also being applied to the monitor 6, is correct. When the instantaneous adjustment in the form of the adjustment parameter vector $\underline{p}_{opt}$ is confirmed by the physician, the adjustment parameter vector $\underline{p}_{akt}$ is stored in the memory 29 and conducted therefrom to the control unit (not shown). At the same time the adjustment of the absorption means, embodied in the adjustment parameter vector $\underline{p}_{opt}$, is superposed on the actual X-ray image in the superposition unit 34.

The adjustment parameter vector $\underline{p}_{akt}$ actually used and stored in the memory 29 is applied to the adaptation unit 30 in which the knowledge base is adapted by means of a learning process.

The use of the quality function calculation will be illustrated on the basis of a simple example.

The image I(x,y) stored in the image memory is subdivided into N non-overlapping, rectangular regions $I_{i(x,y)}$ of a width of $N_x$ pixels and a length of $N_y$ pixels. For these regions the structure contained therein is described by the variance and $$\sigma_i^2 = \frac{1}{(N_x N_y - 1)} \sum_{x=1}^{N_x} \sum_{y=1}^{N_y} \left( I_i(x, y) - \frac{1}{N_x N_y} \sum_{x=1}^{N_x} \sum_{y=1}^{N_y} I_i(x, y) \right)^2 \quad (4)$$

is calculated as the parameter. Because only one parameter is calculated for all image regions, the parameter matrix $\underline{\underline{C}}$ has one row only:

$$\underline{\underline{C}} = (\sigma_1 \ldots \sigma_N)$$

For a single absorption means, hereinafter being a semi-transparent plate whose position is characterized by the adjustment parameter vector $\underline{p}=(1, \Phi\phi)$, with the angle Φ and the insertion length l, the effect of the radiation attenuation on an image I can be represented by a function D($\underline{p}$,x,y) in such a manner that the attenuated image $I_D$ is given by $$I_D(\underline{p}, x, y) = D(\underline{p}, x, y) I(x, y) \quad (5)$$

D($\underline{p}$,x,y) can be approximated, for example, via simple simulations.

For the optimization a quality function Z(r, s, $\underline{\underline{C}}$, D($\underline{p}$)) can be indicated which is dependent on the additional parameter vectors r and s. A simple example of such a quality function can be given by the weighted addition of a plurality of single quality functions; for example, should essentially regions of little structure be removed, a component can penalize the attenuation of diagnostically relevant regions containing structures, that is such structures lead to an increase of the quality function which is then to be minimized. A further component penalizes regions with little structure which are not masked by the inserted diaphragm plate. Such a quality function is, for example, as follows:

$$Z(r, s, \underline{C}, D(\underline{p})) = \sum_{n=1}^{N} (rU(D_n(\underline{p})(1 - c_{1,n}/s^2)) + \qquad (6)$$
$$U((1 - D_n(\underline{p}))(c_{1,n}/s^2 - 1)))$$

where $$D_n = \frac{1}{N_x N_y} \sum_{x=1}^{N_x} \sum_{y=1}^{N_y} D(\underline{p}, x, y) \qquad (7)$$

and the elements of $\underline{\underline{C}}$ are in conformity with $$c_{l,n} = \{\underline{\underline{C}}\}_{l,n}.$$

In the present example the control base has only a single component r; the parameter s represents the sole component of the system parameter vector $\underline{s}$ and provides dose-dependent and radiation quality dependent normalization of the diagnostically relevant contrast. This parameter can be read from a stored table in dependence on the beam quality used. The function U increasingly penalizes positive contributions. It may be given, for example by $$U(x) = \begin{cases} x^2 & \text{for } x > 0 \\ 0 & \text{for } x \leq 0 \end{cases}$$

The first term of the quality function (6) thus penalizes unstructured regions which are not attenuated. The second term of the quality function (6) evaluates the effect of the introduced plate on contrasts in the diagnostically relevant region. Both components are contradictory and are weighted relative to one another via r. The larger r is chosen, the more the suppression of unstructured regions is given priority over the preservation of diagnostically relevant information.

The optimum diaphragm position is then determined by minimizing the quality function:

$$\underline{p}_{opt} = \arg \min_{\underline{p}} Z(r, s, \underline{C}, D(\underline{p})). \qquad (8)$$

This can be performed, for example numerically by way of the Nelder-Mead Simplex algorithm. The diaphragm position thus determined is then graphically superposed on the monitor or adjusted directly by motor. As has already been described, the correction can be used to perform the user-specific or application-specific adaptation of r.

What is claimed is:

1. An X-ray examination apparatus, comprising an x-ray source, an x-ray detector, an absorption means arranged between the x-ray source and the x-ray detector, a control unit for adjusting the degree of absorption of the absorption means, an image processing unit and a display unit, wherein the absorption degree is optimized in dependence upon at least one of user specific parameters (r), apparatus specific parameters (s), structure parameters (C), parameters (R) classifying the subject matter of the image, and further comprising a superposition unit which superposes, prior to the adjustment of the absorption means, a calculated adjustment of the absorption means on an X-ray image to be displayed.

2. An X-ray examination apparatus, comprising an x-ray source, an x-ray detector, an absorption means arranged between the x-ray source and the x-ray detector, a control unit for adjusting the degree of absorption of the absorption means, an image processing unit and a display unit, wherein the absorption degree is optimized in dependence upon at least one of user specific parameters (r), apparatus specific parameters (s), structure parameters (C), parameters (R) classifying the subject matter of the image, and further comprising an adaptation unit for adapting the parameter (r) over several X-ray exposures.

3. An X-ray examination apparatus, comprising an x-ray source, an x-ray detector, an absorption means arranged between the x-ray source and the x-ray detector, a control unit for adjusting the degree of absorption of the absorption means, an image processing unit and a display unit, wherein the absorption degree is optimized in dependence upon at least one of user specific parameters (r), apparatus specific parameters (s), structure parameters (C), parameters (R) classifying the subject matter of the image, and further comprising a parameter extraction unit for receiving the image freed from attenuation and for extracting the parameters which characterize the image.

* * * * *